(12) United States Patent
Shudo

(10) Patent No.: US 10,159,408 B2
(45) Date of Patent: Dec. 25, 2018

(54) DETECTION APPARATUS AND DETECTION METHOD

(71) Applicant: JVC KENWOOD Corporation, Yokohama-shi, Kanagawa (JP)

(72) Inventor: Katsuyuki Shudo, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 170 days.

(21) Appl. No.: 15/272,603

(22) Filed: Sep. 22, 2016

(65) Prior Publication Data

US 2017/0007120 A1 Jan. 12, 2017

Related U.S. Application Data

(63) Continuation of application No. PCT/JP2015/055992, filed on Feb. 27, 2015.

(30) Foreign Application Priority Data

Mar. 25, 2014 (JP) .................................. 2014-062183
Mar. 25, 2014 (JP) .................................. 2014-062184

(51) Int. Cl.
*A61B 3/113* (2006.01)
*A61B 3/00* (2006.01)
(Continued)

(52) U.S. Cl.
CPC ............ *A61B 3/113* (2013.01); *A61B 3/0025* (2013.01); *A61B 3/0058* (2013.01); *A61B 3/14* (2013.01); *A61B 5/16* (2013.01); *G06K 9/00597* (2013.01)

(58) Field of Classification Search
CPC ........... A61B 3/103; A61B 3/113; A61B 3/14; A61B 3/0058; A61B 3/0025; A61B 3/00;
(Continued)

(56) References Cited

U.S. PATENT DOCUMENTS

| 8,371,693 B2 | 2/2013 | Ebisawa | |
|---|---|---|---|
| 2008/0186449 A1* | 8/2008 | Sur | ........................ A61B 3/113 351/210 |

(Continued)

FOREIGN PATENT DOCUMENTS

| EP | 2965689 A1 | 1/2016 |
|---|---|---|
| JP | 8-238222 | 9/1996 |

(Continued)

OTHER PUBLICATIONS

English translation of JP 2014-18484, machine translated on Apr. 2, 2018.*

(Continued)

*Primary Examiner* — Jie Lei
(74) *Attorney, Agent, or Firm* — Amin, Turocy & Watson LLP

(57) ABSTRACT

Provided is a detection apparatus and detection method. The detection apparatus includes an imaging unit that images a subject and an eye gaze detector detects the subject's eye gaze direction based on a captured image. A diagnostic image is displayed that includes an image including a face image and a geometric pattern image. A first gaze point is detected as a gaze point of the subject in the person image based on the eye gaze direction and a second gaze point is detected as a gaze point of the subject in a determination region in the geometric pattern image.

6 Claims, 15 Drawing Sheets

(51) Int. Cl.
*A61B 5/16* (2006.01)
*A61B 3/14* (2006.01)
*G06K 9/00* (2006.01)

(58) Field of Classification Search
CPC ... A61B 3/1208; A61B 3/1225; A61B 3/1015;
A61B 5/16; G06K 9/00597; G06K
9/00228; G06T 2207/10016
USPC ....... 351/206, 205, 209, 210, 220, 221, 246;
382/103, 117, 118
See application file for complete search history.

(56) References Cited

U.S. PATENT DOCUMENTS

2015/0050628 A1 2/2015 Mori et al.
2015/0374223 A1* 12/2015 Shudo .................. A61B 3/113
351/210

FOREIGN PATENT DOCUMENTS

| | | |
|---|---|---|
| JP | 2005-198743 | 7/2005 |
| JP | 2011-206542 | 10/2011 |
| JP | 2013-052116 | 3/2013 |
| JP | 2013-223713 | 10/2013 |
| JP | 2014-018484 | 2/2014 |
| WO | 2008/097933 A1 | 8/2008 |

OTHER PUBLICATIONS

Extended European Search Report for European Patent Application No. 15768199.0 dated Feb. 27, 2017.
International Search Report for International Patent Application No. PCT/JP2015/055992 dated May 12, 2015, 4 pages.
Written Opinion for International Patent Application No. PCT/JP2015/055992 dated May 12, 2015, 4 pages.
Pierce K et al., Preference for Geometric Patterns Early in Life as a Risk Factor for Autism, Arch Gen Psychiatry, Jan. 2011; 68 (1): 101-109.

* cited by examiner

# DETECTION APPARATUS AND DETECTION METHOD

CROSS-REFERENCE TO RELATED APPLICATION

This application is a continuation of PCT international application Ser. No. PCT/JP2015/055992 filed on Feb. 27, 2015 which designates the United States, incorporated herein by reference, and which claims priority to and incorporates by reference the entire contents of Japanese Patent Application No. 2014-062183 filed in Japan on Mar. 25, 2014 and Japanese Patent Application No. 2014-062184 filed in Japan on Mar. 25, 2014.

FIELD

The present invention relates to a detection apparatus and a detection method.

BACKGROUND

Recently, persons with developmental disorder are said to be on the rise. It has been found that detecting symptoms and starting medical treatment in an early stage can alleviate symptoms of the developmental disorder and enhance effects to adapt to the society. In Japan, efforts are encouraged to find the developmental disorder at an early stage by an interview at the time of medical checkup for half-past-one-year-old children, or the like. However, the effect is not enough because there are problems such as shortage of psychiatrists and an increased length of time for the interview. To cope with this, there is a demand for an objective and efficient diagnosis assistance apparatus for the developmental disorder.

To find the developmental disorder at an early stage, for example, it is ideal that the diagnosis is possible at the time of medical checkup for half-past-one-year-old children. Also, care need to be paid when the apparatus is used at the medical checkup. A typical behavior of the developmental disorder children is to avoid looking at eyes of a person facing them (turn their eyes away). It is also known as a typical behavior of developmental disorder children that they favor a video of a geometric pattern rather than a video of a person. There is a technique for detecting a gaze point by imaging a face of a person by a camera and calculating positions of a corneal reflection and a pupil, and thus, methods for assisting the diagnosis of developmental disorder by applying this technique, or the like, are proposed.

As described above, even with known techniques for detecting a gaze point and techniques for assisting diagnosis of a subject with developmental disorder, there are further demands for a method for detecting with higher accuracy.

In view of the above, it is an object of the present invention to provide a detection apparatus and a detection method capable of achieving improved detection accuracy.

In one aspect, there is provided a detection apparatus comprising: a display; an imaging unit configured to image a subject; an eye gaze detector configured to detect an eye daze direction of the subject based on a captured image captured by the imaging unit; an output controller configured to display a diagnostic image that includes a person image and a geometric pattern image, onto the display; and a gaze point detector configured to detect a first gaze point as a gaze point of the subject in the person image based on the eye gaze direction, and configured to detect a second gaze point as a gaze point of the subject in a region that includes at least one of a center of a geometric pattern, a characteristic portion of the geometric pattern, a portion in which density of lines forming the geometric pattern is higher than other portions, and a portion in which the geometric pattern changes, in the geometric pattern image.

A detection apparatus and a detection method according to the present invention can effectively improve detection accuracy.

DESCRIPTION OF EMBODIMENTS

Hereinafter, a detection apparatus and a detection method according to embodiments of the present invention will be described in detail with reference to the drawings. Note that the present invention is not limited by these embodiments. Hereafter, an exemplary application of a detection apparatus as a diagnosis assistance apparatus to assist diagnosis of developmental disorder, or the like, based on a result of eye gaze detection will be described. An applicable apparatus is not limited to the diagnosis assistance apparatus.

The detection apparatus (diagnosis assistance apparatus) according to the present embodiment detects an eye gaze by using an illuminator disposed at a single position. The detection apparatus (diagnosis assistance apparatus) according to the present embodiment calculates a corneal curvature center position with high accuracy based on a result of a measurement performed before the eye gaze detection while having a subject gaze at a point.

Note that the illuminator is a component that includes a light source and can illuminate an eyeball of the subject with light. The light source is a light emitting device, for example, a light emitting diode (LED). The light source may be formed of one LED or a plurality of LEDs in combination to be disposed at one position. Hereafter, a "light source" may be used as above as a term to indicate the illuminator.

It is also appropriate to configure such that an eye gaze is detected by using illuminators disposed at two or more positions. In this case, for example, an eye gaze detection method similar to the technique in Patent Literature 2 can be applied.

Figure 1:
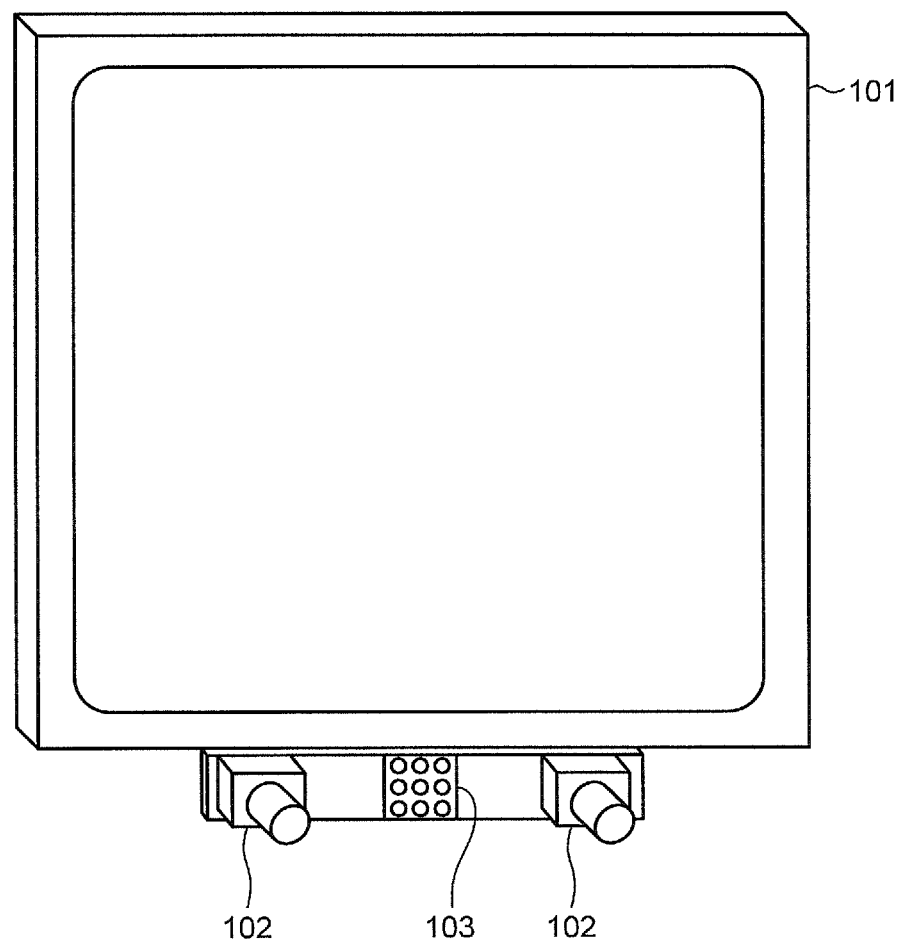
FIG. 1 is a diagram illustrating an exemplary arrangement of a display, a stereo camera, an infrared light source, and a subject according to the present embodiment.
Figure 2:
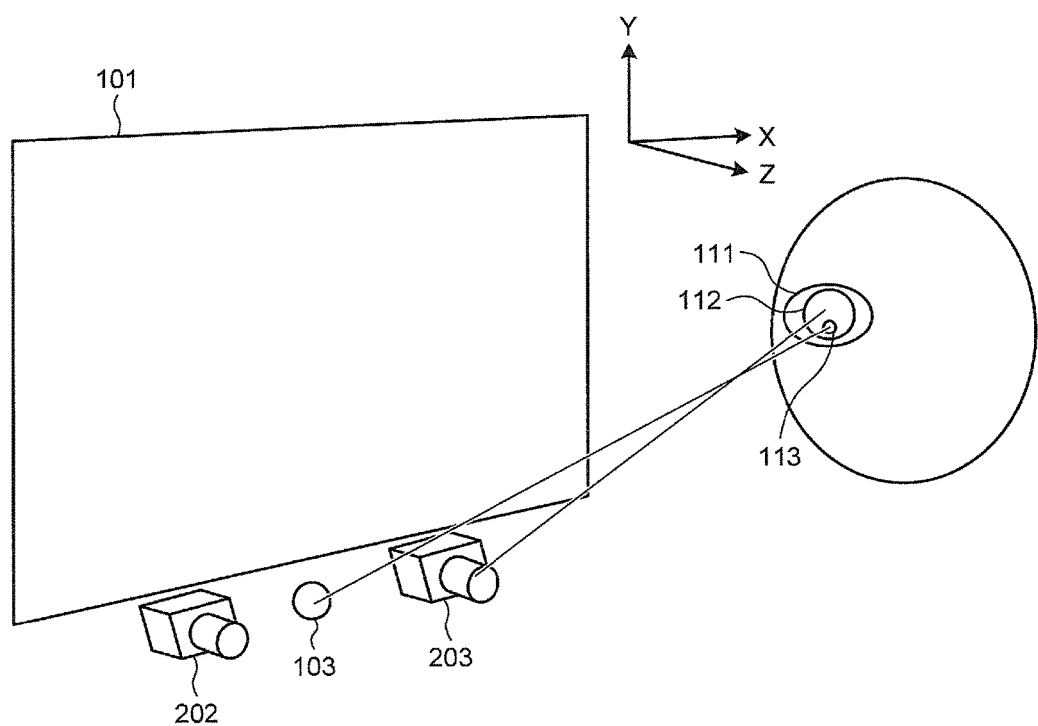
FIG. 2 is a diagram illustrating an exemplary arrangement of a display, a stereo camera, an infrared light source, and a subject according to the present embodiment.

FIGS. 1 and 2 are diagrams illustrating exemplary configurations of a display, a stereo camera, an infrared light source, and the subject according to the present embodiment.

As illustrated in FIG. 1, the diagnosis assistance apparatus according to the present embodiment includes a display 101, a stereo camera 102, and an LED light source 103. The stereo camera 102 is disposed beneath the display 101. The LED light source 103 is disposed at a center position of two cameras included in the stereo camera 102. The LED light source 103 is a light source for emitting, for example, near-infrared light with a wavelength of 850 nm. FIG. 1 illustrates an exemplary configuration of the LED light source 103 (illuminator) formed of nine LEDs. The stereo camera 102 includes a lens that can transmit near-infrared light with a wavelength of 850 nm.

As illustrated in FIG. 2, the stereo camera 102 includes a right camera 202 and a left camera 203. The LED light source 103 emits near-infrared light toward an eyeball 111 of the subject. In an image obtained by the stereo camera 102, a pupil 112 is darkened by low-luminance reflection and a corneal reflection 113 generated inside the eyeball 111 as a virtual image is brightened with high-luminance reflection. Accordingly, on-image positions of the pupil 112 and the corneal reflection 113 can be obtained by the two cameras (right and left cameras 202 and 203) respectively.

Based on the positions of the pupil 112 and the corneal reflection 113 obtained by the two cameras, three-dimensional world coordinate values for the positions of the pupil 112 and the corneal reflection 113 are calculated. The present embodiment defines three-dimensional world coordinates such that a Y-coordinate represents a height (upper direction is indicated by +), an X-coordinate represents a width (right-hand direction is indicated by +), and a Z-coordinate represents a depth (front direction is indicated by +), with respect to a center position of the screen of the display 101 as an origin.

Figure 3:
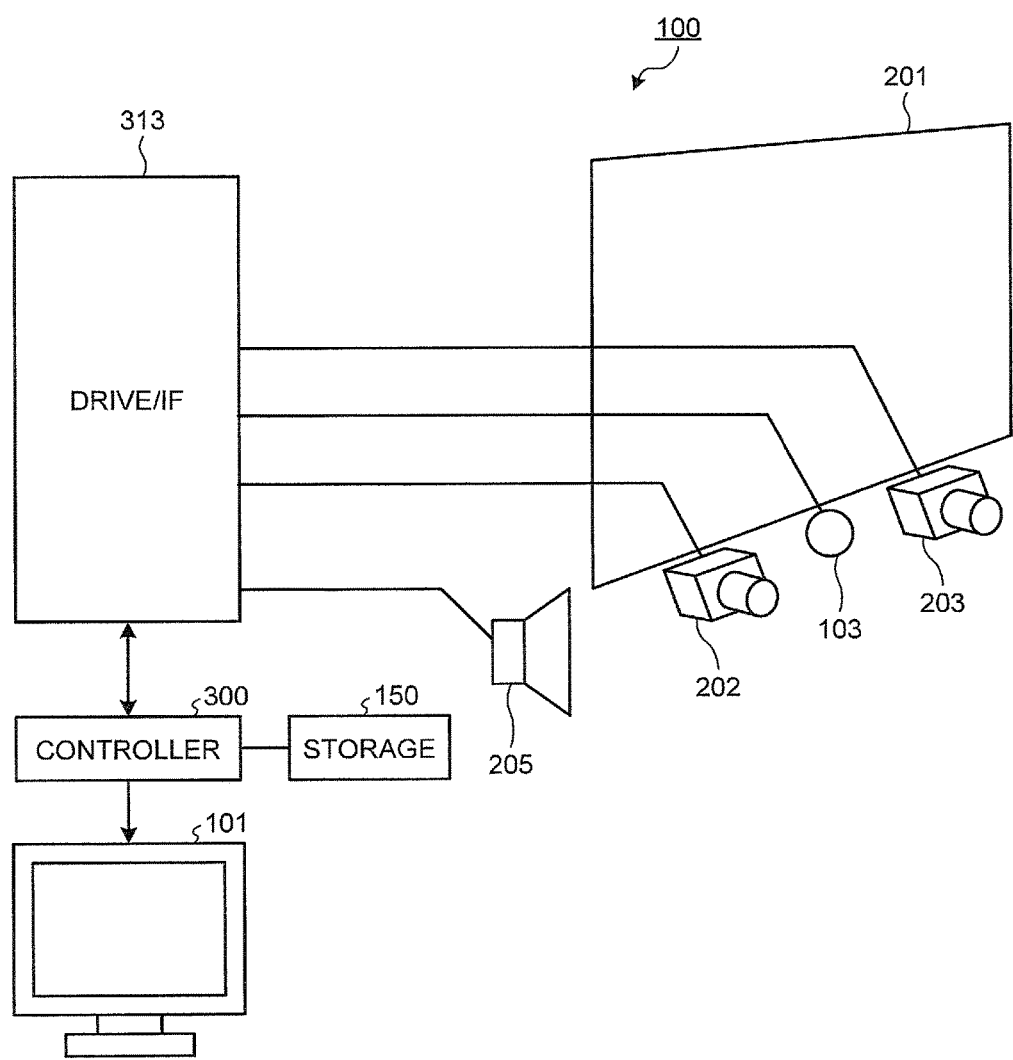
FIG. 3 is a schematic diagram illustrating a function of a diagnosis assistance apparatus.

FIG. 3 is a functional schematic diagram of a diagnosis assistance apparatus 100. FIG. 3 illustrates a part of the configurations illustrated in FIGS. 1 and 2, and the configurations to be used for driving, or the like, in this configuration. As illustrated in FIG. 3, the diagnosis assistance apparatus 100 includes the right camera 202, the left camera 203, the LED light source 103, a speaker 205, a drive/interface (IF) unit 313, a controller 300, a storage 150, and the display 101. In FIG. 3, a display screen 201 clearly indicates the positional relationship between the right and left cameras 202 and 203. The display screen 201 is a screen displayed on the display 101. The drive unit and the IF unit may be disposed in combination or separately.

The speaker 205 functions as an audio output unit that outputs voice, etc. for alerting the subject at calibration, or the like.

The drive/IF 313 drives each of components of the stereo camera 102. The drive/IF 313 also functions as an interface between each of the components of the stereo camera 102 and the controller 300.

The controller 300 can be implemented, for example, by a computer including a control apparatus such as a central processing unit (CPU), a storage apparatus such as a read only memory (ROM) and a random access memory (RAM), a communication I/F to perform communication via a connected network, and a bus to connect individual units.

The storage 150 stores various information such as a control program, a measurement result, and a diagnosis assistance result. The storage 150 stores, for example, an image to be displayed on the display 101. The display 101 displays various information such as a target image for diagnosis.

Figure 4:
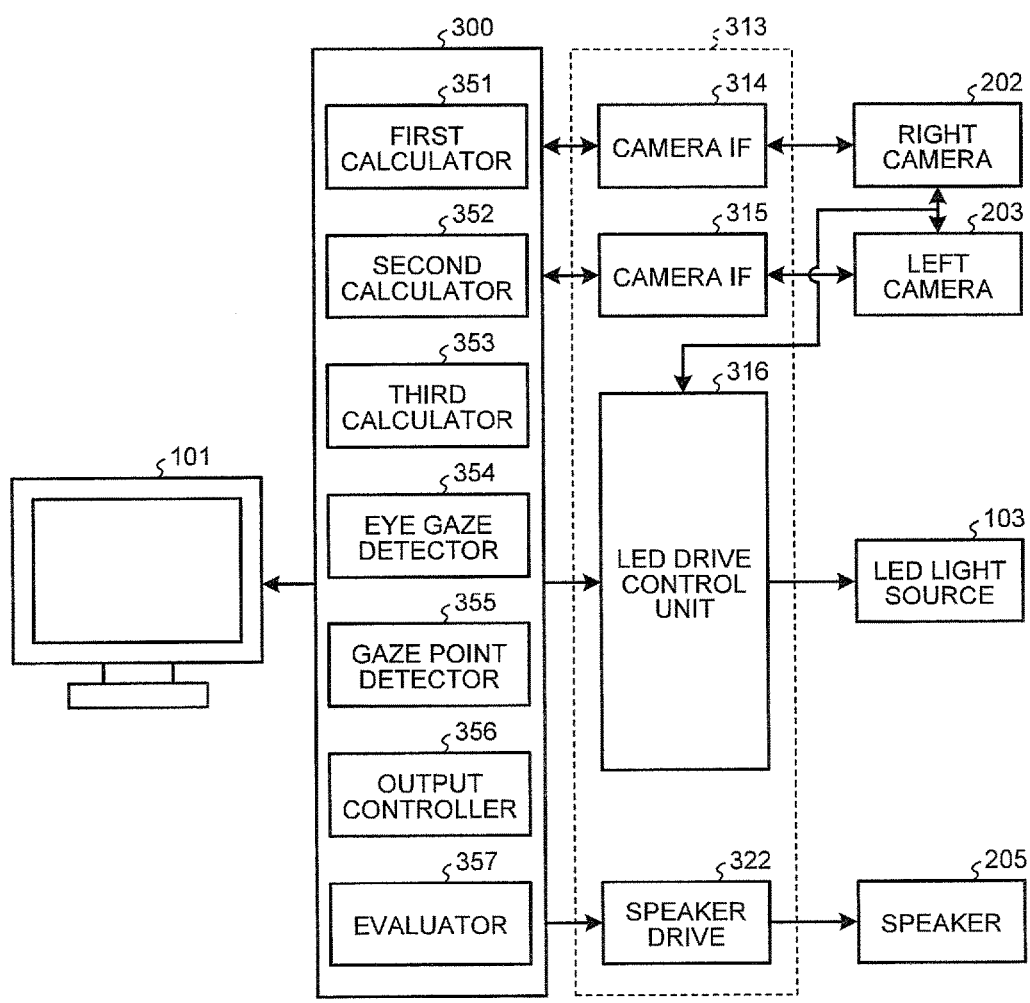
FIG. 4 is a block diagram illustrating an exemplary detailed function of each of components illustrated in FIG. 3.

FIG. 4 is a block diagram illustrating an exemplary detailed function of each of components illustrated in FIG. 3. As illustrated in FIG. 4, the display 101 and the drive/IF 313 are connected to the controller 300. The drive/IF 313 includes camera IFs 314 and 315, an LED drive control unit 316, and a speaker drive 322.

The right and left cameras 202 and 203 are connected to the drive/IF 313 via the camera IFs 314 and 315, respectively. The drive/IF 313 drives these cameras to image the subject.

The speaker drive 322 drives the speaker 205. The diagnosis assistance apparatus 100 may include an interface (printer IF) for connecting with a printer as a printing unit. The printer may be provided inside the diagnosis assistance apparatus 100.

The controller 300 controls the overall diagnosis assistance apparatus 100. The controller 300 includes a first calculator 351, a second calculator 352, a third calculator 353, an eye gaze detector 354, a gaze point detector 355, an output controller 356, and an evaluator 357. Note that for the eye gaze detection apparatus, it would be sufficient that at least the first calculator 351, the second calculator 352, the third calculator 353, and the eye gaze detector 354 are provided.

Each of the components included in the controller 300, namely, the first calculator 351, the second calculator 352, the third calculator 353, the eye gaze detector 354, the gaze point detector 355, the output controller 356, and the evaluator 357, may be implemented as software (program) and/or a hardware circuit.

In the case of implementation as a program, the program is provided as a computer program product as a file in an installable form or an executable form, stored on a computer-readable recording medium such as a compact disk read only memory (CD-ROM), a flexible disk (FD), a compact disk recordable (CD-R), and a digital versatile disk (DVD). The program may be stored on a computer connected to a network such as the Internet and may be downloaded and provided via the network. Alternatively, the program may be provided or distributed via the network such as the Internet. Also, the program may be stored in a ROM, etc. in advance and provided.

The first calculator 351 calculates a pupil center position (first position) indicating a center of the pupil based on the image of the eyeball captured by the stereo camera 102. The second calculator 352 calculates a corneal reflection center position (second position) indicating a center of the corneal reflection based on the captured image of the eyeball.

The third calculator 353 calculates a corneal curvature center (third position) based on a line that connects the LED light source 103 with the corneal reflection center position. For example, the third calculator 353 calculates, as the corneal curvature center, a position where a distance from the corneal reflection center on this line is equal to a predetermined value. The predetermined value may be a value determined beforehand based on an ordinary corneal curvature radius value, or the like.

Since the corneal curvature radius value might include an individual variation, calculating the corneal curvature center based on the predetermined value might cause a large error. Therefore, the third calculator 353 may calculate the corneal curvature center in view of the individual variation. In this case, by using the pupil center and the corneal reflection center, both of which have been calculated with the subject gazing at a target position, the third calculator 353 calculates an intersection of a line (fourth position) that connects the pupil center with the target position and the line that connects the corneal reflection center with the LED light source 103. The third calculator 353 calculates a distance (first distance) between the pupil center and the calculated intersection and stores the distance in the storage 150, for example.

The target position only needs to be a predetermined position by which the three-dimensional world coordinate values can be calculated. For example, a center position on the display screen 201 (origin of the three-dimensional world coordinates) may be determined as the target position. In this case, for example, the output controller 356 displays an image (target image) etc. that can obtain the gaze of the subject, at the target position (center) on the display screen 201. This can lead the subject to gaze at the target position.

The target image may be any image that can attract the attention of the subject. For example, an image having a variable display aspect such as luminance or color and an image having a distinctive display aspect compared with other regions can be used as the target image.

Note that the target position need not be at the center of the display screen 201 but may be at any position. When the center of the display screen 201 is determined as the target position, the distance to any end portion of the display screen 201 is minimized. Accordingly, a measurement error at the eye gaze detection can be reduced, for example.

Processing up to the calculation of the distance is assumed to have been executed, for example, before a start of an actual eye gaze detection. At actual execution of the eye gaze detection, the third calculator 353 calculates, as the corneal curvature center, the position on the line that connects the LED light source 103 with the corneal reflection center where the distance from the pupil center equals the distance calculated beforehand.

The eye gaze detector 354 detects an eye gaze of the subject based on the pupil center and the corneal curvature center. The eye gaze detector 354 detects, for example, a direction from the corneal curvature center to the pupil center as an eye gaze direction of the subject.

The gaze point detector 355 detects the gaze point of the subject using the detected eye gaze direction. The gaze point detector 355 detects, for example, the gaze point (point of gaze), the point at which the subject gazes on the display screen 201. The gaze point detector 355 detects, as the gaze point of the subject, an intersection of an eye gaze vector and an X-Y plane, expressed in the three-dimensional world coordinates as illustrated in FIG. 2, for example.

The output controller 356 controls output of various information to the display 101, the speaker 205, or the like.

For example, the output controller 356 outputs the target image at the target position on the display 101. The output controller 356 also controls the output to the display 101, of a diagnostic image and an evaluation result from the evaluator 357, or the like.

The diagnostic image may be any image corresponding to evaluation processing based on the eye gaze (gaze point) detection result. In diagnosing developmental disorder, for example, it is appropriate to use the diagnostic images including an image favored by the subject with the developmental disorder (geometric pattern image, etc.) as well as another image (person image, etc.). The image may be either a still image or a moving image. The geometric pattern image is, for example, an image including one or more geometric patterns. The person image may be, for example, an image including a face of a person. It is also appropriate to use an image on which a person exist on an image (still image or moving image) obtained by imaging an animal, plant, natural scene or the like, with camera. It is also appropriate to use an image (still image or moving image) of a character imitating a person, or the like.

The evaluator 357 executes the evaluation processing based on the diagnostic image and the gaze point detected by the gaze point detector 355. In diagnosing developmental disorder, for example, the evaluator 357 analyzes the diagnostic image and the gaze point and evaluates whether the subject with the developmental disorder has gazed at his/her favored image.

Figure 5:
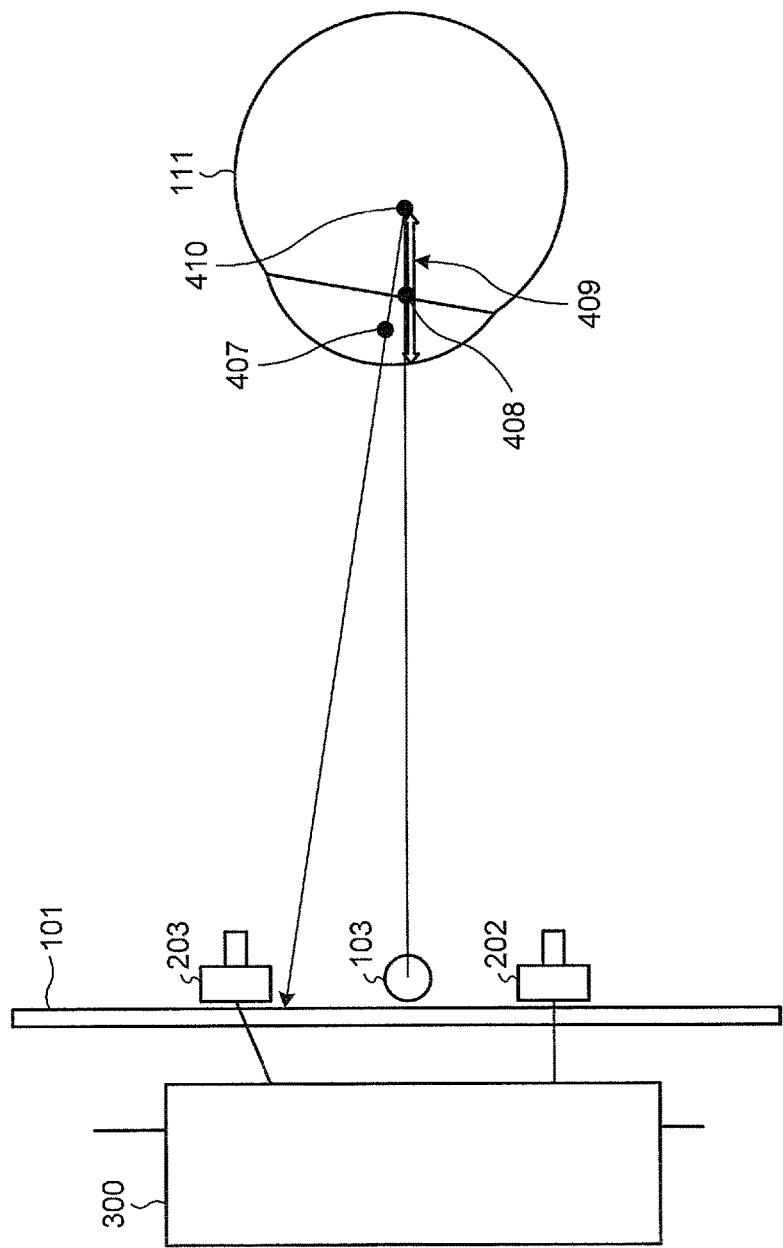
FIG. 5 is a schematic diagram illustrating processing to be executed by a diagnosis assistance apparatus according to the present embodiment.

FIG. 5 is a schematic diagram illustrating processing to be executed by the diagnosis assistance apparatus 100 according to the present embodiment. The same reference signs are given to the components described in FIGS. 1 to 4 and the description thereof will be omitted.

A pupil center 407 and a corneal reflection center 408 represent a pupil center and a corneal reflection point center, respectively, each being detected when the LED light source 103 is lit. A corneal curvature radius 409 represents a distance from a corneal surface to a corneal curvature center 410.

Figure 6:
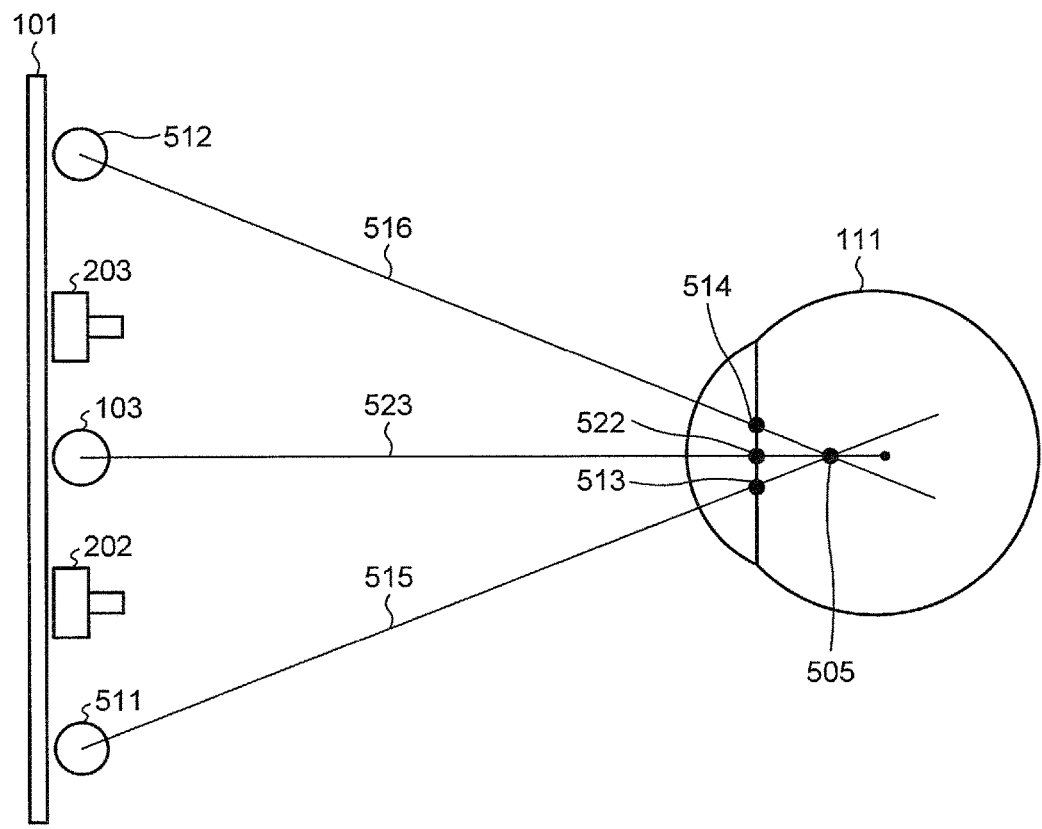
FIG. 6 is a diagram illustrating a difference between a method of using two light sources and the present embodiment using one light source.

FIG. 6 is a diagram illustrating a difference between a method (hereinafter, referred to as a method A) using two light sources (illuminators) and the present embodiment using one light source (illuminator). The same reference signs are given to the components described in FIGS. 1 to 4 and the description thereof will be omitted. Connection between left and right cameras (right camera 202/left camera 203) and the controller 300 will be omitted without illustration.

The method A uses two LED light source 511 and 512 instead of the LED light source 103. The method A calculates an intersection of a line 515 that connects a corneal reflection center 513 with the LED light source 511 when the LED light source 511 is lit, and a line 516 that connects a corneal reflection center 514 with the LED light source 512 when the LED light source 512 is lit. This intersection corresponds to a corneal curvature center 505.

In contrast, the present embodiment discusses a line 523 that connects a corneal reflection center 522 with the LED light source 103 when the LED light source 103 is lit. The line 523 passes through the corneal curvature center 505. It is known that the corneal curvature radius is less affected by individual variation and has substantially a fixed value. From this fact, the corneal curvature center when the LED light source 103 is lit exists on the line 523 and can be calculated using an ordinary curvature radius value.

However, when the gaze point is calculated using a corneal curvature center position obtained by using the ordinary curvature radius value, the gaze point position cannot be detected correctly, in some cases, because of deviation of the gaze point position from the original position due to individual variation in eyeballs.

Figure 7:
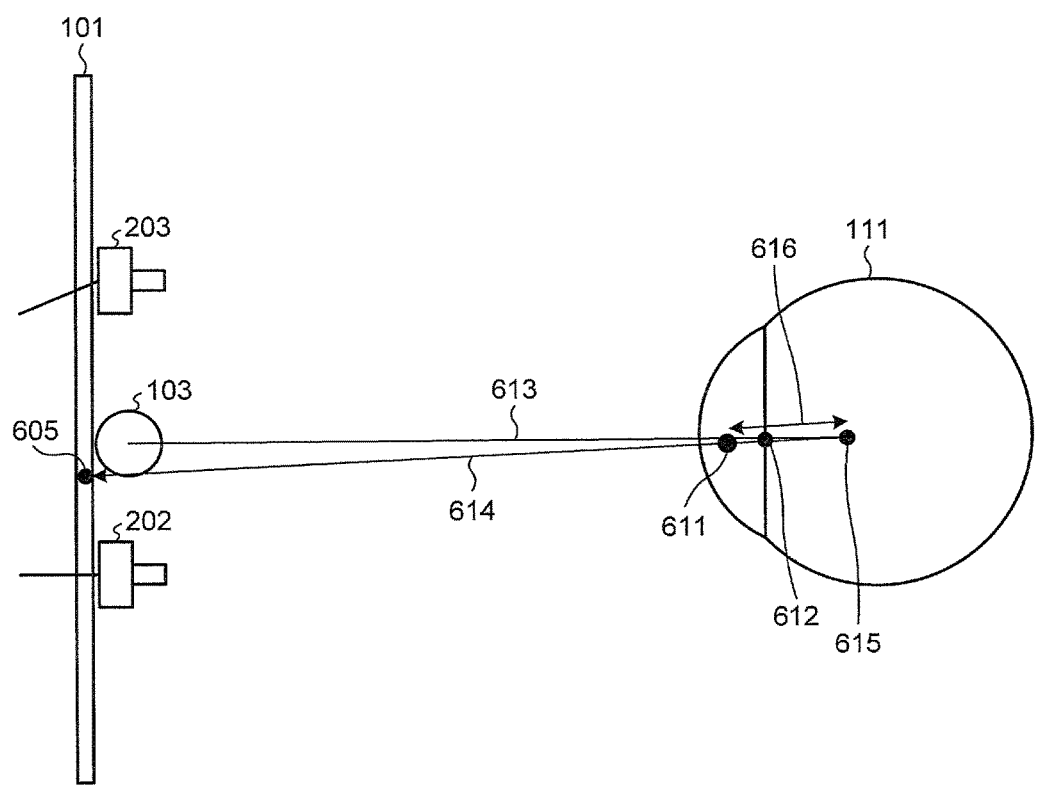
FIG. 7 is a diagram illustrating calculation processing to calculate a distance between a pupil center position and a corneal curvature center position.

FIG. 7 is a diagram illustrating calculation processing for calculating the position of the corneal curvature center, and calculating the distance between the pupil center position and the corneal curvature center position. This calculation processing is executed before gaze point detection (eye gaze detection). The same reference signs are given to the components described in FIGS. 1 to 4 and the description thereof will be omitted.

A target position 605 is a position to obtain the gaze of the subject by displaying the target image, etc. at a point on the display 101. In the present embodiment, the target position 605 is assumed to be at the center position of the screen of the display 101. A line 613 is a line that connects the LED light source 103 with a corneal reflection center 612. A line 614 is a line that connects the target position 605 (gaze point) at which the subject gazes with a pupil center 611. A corneal curvature center 615 is an intersection of the line 613 and the line 614. The third calculator 353 calculates and stores a distance 616 between the pupil center 611 and the corneal curvature center 615.

Figure 8:
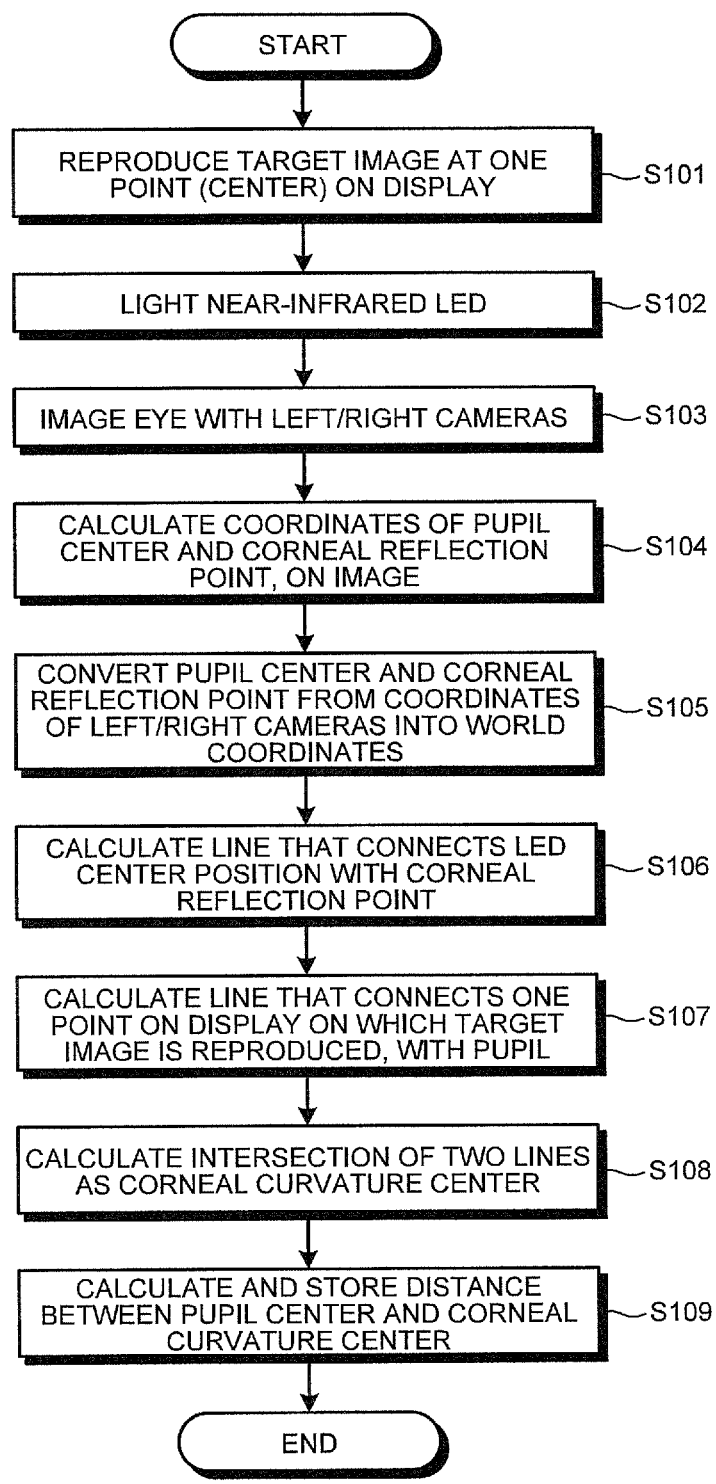
FIG. 8 is a flowchart illustrating exemplary calculation processing according to the present embodiment.

FIG. 8 is a flowchart illustrating exemplary calculation processing according to the present embodiment.

The output controller 356 initially reproduces the target image at a point on the screen of the display 101 (step S101) and leads the subject to gaze at the point. Next, by operating the LED drive control unit 316, the controller 300 causes the LED light source 103 to be lit toward the eye of the subject (step S102). The controller 300 images (step S103) the eye of the subject by the left and right cameras (right camera 202/left camera 203).

Under the illumination from the LED light source 103, a pupil portion is detected as a dark portion (dark pupil). In addition, a virtual image of the corneal reflection is generated as a reflection of the LED illumination, and the corneal reflection point (corneal reflection center) is detected as a bright portion. That is, the first calculator 351 detects the pupil portion from the captured image and calculates the coordinates indicating the pupil center position. The second calculator 352 also detects a corneal reflection portion from the captured image and calculates the coordinates indicating the corneal reflection center position. In addition, each of the first calculator 351 and the second calculator 352 calculates each of coordinate values of the two images captured by the left and right cameras (step S104).

Meanwhile, in order to obtain the three-dimensional world coordinates, the left and right cameras have undergone camera calibration using a stereo calibration method in advance, and thereby the conversion parameter has been calculated. As the stereo calibration method, any conventional method such as the method using the Tsai camera calibration theory is applicable.

The first calculator 351 and the second calculator 352 uses this conversion parameter to convert the coordinates of the left and right cameras into the three-dimensional world coordinates of the pupil center and the corneal reflection center (step S105). The third calculator 353 calculates the line that connects the world coordinates of the obtained corneal reflection center with the world coordinates of the center position of the LED light source 103 (step S106). Next, the third calculator 353 calculates the line that connects the world coordinates of the center of the target image displayed at a point on the screen of the display 101 with the world coordinates of the pupil center (step S107). The third calculator 353 calculates an intersection of the line calculated at step S106 and the line calculated at step S107, and determines this intersection as the corneal curvature center (step S108). The third calculator 353 calculates a distance between the pupil center and the corneal curvature center at this time and stores the distance in the storage 150, or the like (step S109). The stored distance is used later in the gaze point (eye gaze) detection for calculating the corneal curvature center.

In the calculation processing, the distance between the pupil center and the corneal curvature center during the gaze at a point on the display 101 is kept constant in a range of detection of the gaze point in the display 101. The distance between the pupil center and the corneal curvature center may be calculated based on an average of all or some of the values that have been calculated during the reproduction of the target image.

Figure 9:
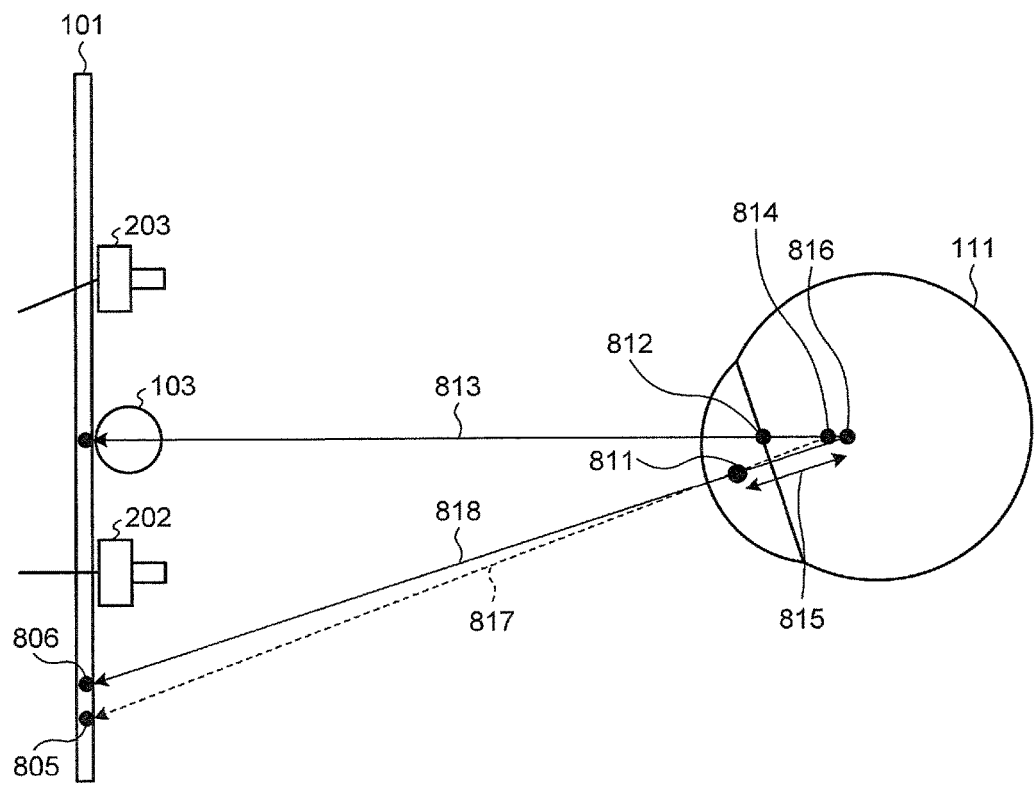
FIG. 9 is a diagram illustrating a method for calculating a corneal curvature center position based on a distance obtained beforehand.

FIG. 9 is a diagram illustrating a method, in the gaze point detection, for calculating a corrected position of the corneal curvature center based on the distance between the pupil center and the corneal curvature center obtained beforehand. A gaze point 805 represents a gaze point obtained from the corneal curvature center calculated based on an ordinary curvature radius value. A gaze point 806 represents a gaze point obtained from the corneal curvature center calculated based on the distance obtained beforehand.

A pupil center 811 and a corneal reflection center 812 correspond to the pupil center position and the corneal reflection center position, respectively, each calculated in the gaze point detection. A line 813 is a line that connects the LED light source 103 with the corneal reflection center 812. A corneal curvature center 814 is a corneal curvature center position calculated from an ordinary curvature radius value. A distance 815 is a distance between the pupil center and the corneal curvature center, which are calculated in the calculation processing performed beforehand. A corneal curvature center 816 represents a position of the corneal curvature center calculated using the distance calculated beforehand. The corneal curvature center 816 can be calculated based on the fact that the corneal curvature center exists on the line 813 and the distance between the pupil center and the corneal curvature center is equal to the distance 815. Accordingly, an eye gaze 817 calculated by using an ordinary curvature radius value is corrected into an eye gaze 818. Also, the gaze point on the screen of the display 101 is corrected from the gaze point 805 to the gaze point 806. Description and diagrams on connection between the left and right cameras (right camera 202/left camera 203) and the controller 300 will be omitted.

Figure 10:
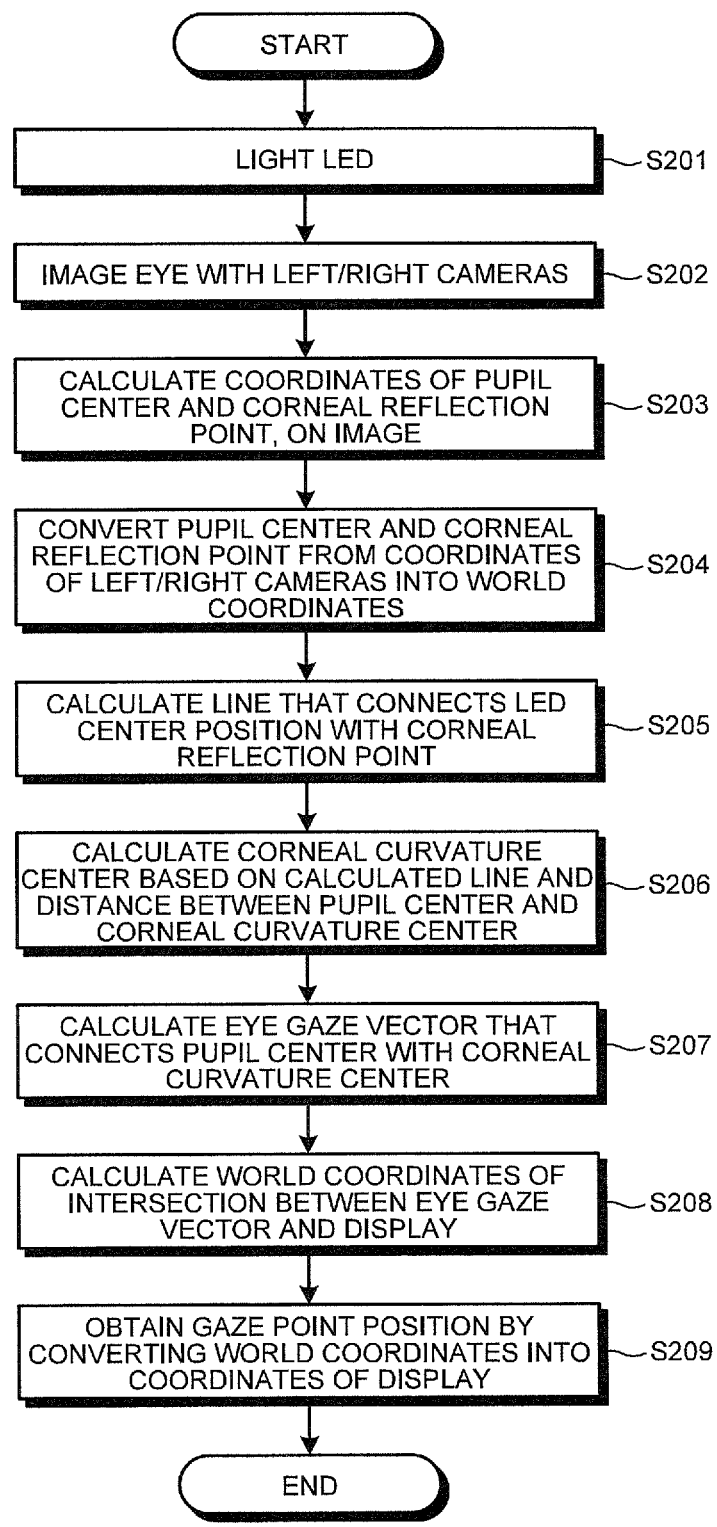
FIG. 10 is a flowchart illustrating exemplary eye gaze detection processing according to the present embodiment.

FIG. 10 is a flowchart illustrating exemplary eye gaze detection processing according to the present embodiment. For example, the eye gaze detection processing in FIG. 10 is executable as processing to detect the eye gaze among diagnostic processing using a diagnostic image. The diagnostic processing also includes, other than the steps illustrated in FIG. 10, processing of displaying the diagnostic image and evaluation processing performed by the evaluator 357 using the detection result of the gaze point.

Since steps S201 to S205 are similar to steps S102 to S106 illustrated in FIG. 8, the description thereof will be omitted.

The third calculator 353 calculates, as the corneal curvature center, the position located on the line calculated at step S205 and where the distance from the pupil center is equal to the distance obtained by the calculation processing performed beforehand (step S206).

The eye gaze detector 354 calculates a vector (eye gaze vector) that connects the pupil center with the corneal curvature center (step S207). This vector represents the eye gaze direction in which the subject is viewing. The gaze point detector 355 calculates the three-dimensional world coordinate values of the intersection between the eye gaze direction and the screen of the display 101 (step S208). This value is the coordinate value, represented by the world coordinate, of the point at which the subject gazes on the display 101. The gaze point detector 355 converts the calculated three-dimensional world coordinate values into the coordinate values (x, y) represented by the two-dimensional coordinate system of the display 101 (step S209). This enables calculating the gaze point (point of gaze) at which the subject gazes on the display 101.

Figure 11:
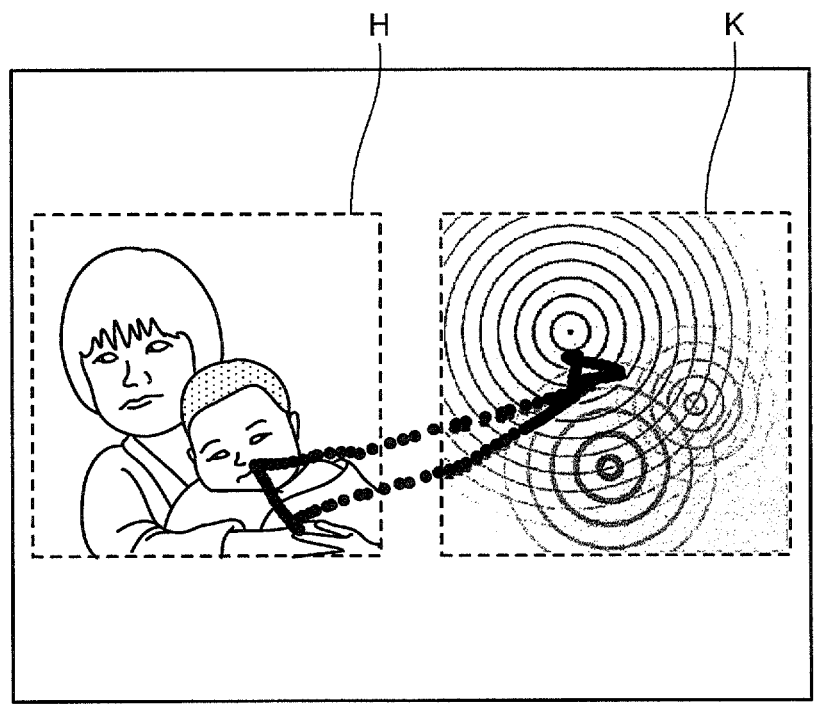
FIG. 11 is a diagram illustrating an exemplary diagnostic image.

Next, details of the diagnosis assistance processing will be described. As a method for diagnosis assistance, there is a method, for example, of using a diagnostic image on which a person image and a geometric pattern image are arranged side by side in left/right positions, and totaling the time of the gaze at a portion in an area (region) of each of left and right images. FIG. 11 is a diagram illustrating an exemplary diagnostic image displayed by this method. A diagnostic image is displayed at around a central area on the display screen 201. This diagnostic image includes a person image (area H) on the left and a geometric pattern image (area K) on the right. For the whole area H and the whole area K, retention time for the gaze points are individually measured. With this method, however, in a case where the eye gaze accidentally falls on an end portion of the area H with no gaze on face portions in the person image (area H), for example, it might be judged that the person image has attracted the gaze.

To cope with this, in the present embodiment, a partial region (area) suitable for diagnosis assistance is provided for each of the person image and the geometric pattern image. Diagnosis assistance is performed by detecting the time during which these portions are attracting the gaze and by comparing the detected time with each other. For example, a determination area (first identification region) is provided at a face portion on the person image, and a determination area (second identification region) is provided at a central portion of the geometric pattern. Determination is performed based on the gazing time for individual determination areas. With this method, in a case where the face portion of a person has attracted gaze with particularly high attention, or in a case where the center of the geometric pattern has attracted the gaze with high attention, the gazing time difference between a neurotypical subject and a subject with developmental disorder becomes more significant. As a result, it is possible to achieve detection with higher accuracy.

Figure 12:
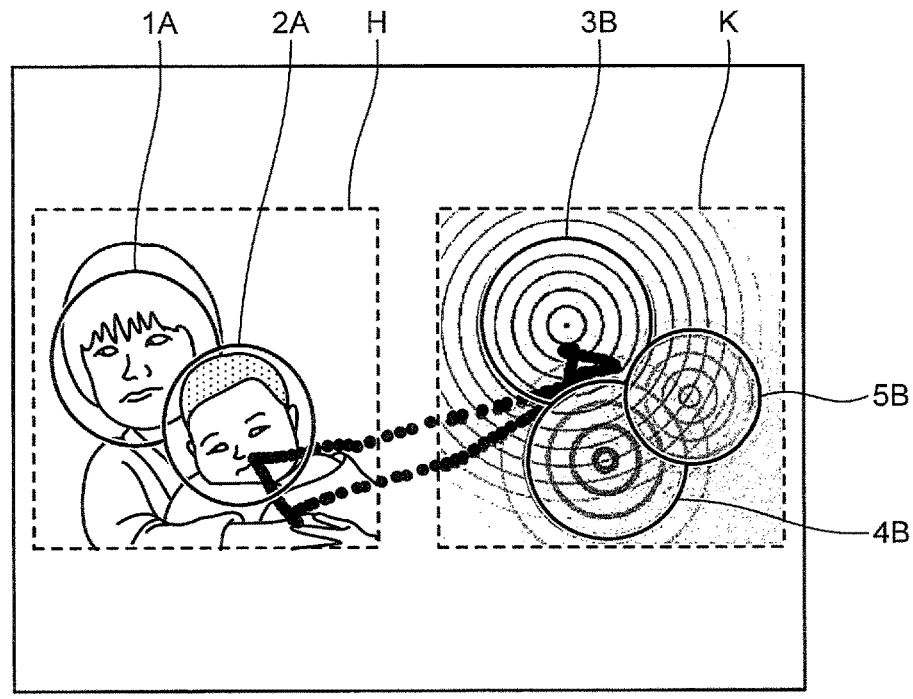
FIG. 12 is a diagram illustrating an exemplary diagnostic image used in the present embodiment.

FIG. 12 is a diagram illustrating an exemplary diagnostic image used in the present embodiment. Similarly to FIG. 11, a diagnostic image is displayed around a central area on the display screen 201. This diagnostic image includes a person image (area H) on the left and includes a geometric pattern image (area K) on the right. According to the present embodiment, more specific determination area is provided in each of the person image and the geometric pattern image. For example, the area H includes an area 1A and an area 2A as determination areas. The area K includes an area 3B, an area 4B, and an area 5B, as determination areas.

The area 1A is an area including a face of a first person (girl). The area 2A is an area including a face of a second person (baby). The area 3B is an area including a center of the geometric pattern at an upper left portion among three geometric patterns within the area K. The area 4B is an area including a center of the geometric pattern at the bottom. The area 5B is an area including a center of the geometric pattern at the center on the right.

In a case where measurement is performed to determine whether the subject is interested in a person or a geometric pattern, at least one of the area 1A and the area 2A is to be used as an area for determining that the subject is interested in a person. Additionally, at least one of the area 3B, the area 4B, and the area 5B is to be used as an area for determining that the subject is interested in a geometric pattern.

Figure 13:
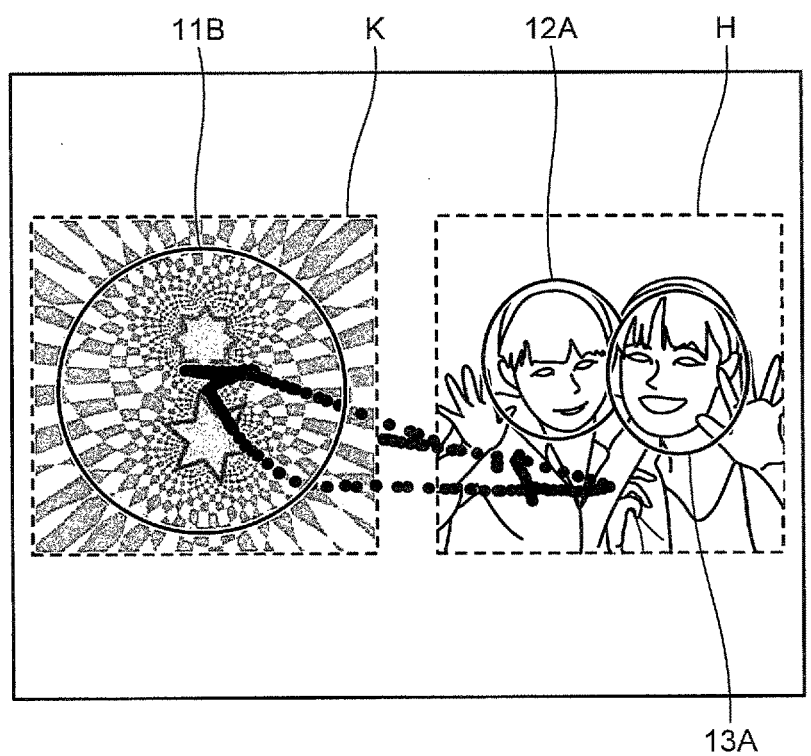
FIG. 13 is a diagram illustrating another exemplary diagnostic image used in the present embodiment.

FIG. 13 is a diagram illustrating another exemplary diagnostic image used in the present embodiment. In an example in FIG. 13, the area H includes an area 12A and an area 13A as determination areas. The area K includes an area 11B as a determination area. FIG. 13 is an exemplary diagnostic image in which arrangement of the person image (area H) and the geometric pattern image (the area K) differs from the arrangement in FIG. 12. In other words, the left portion represents the geometric pattern (area K) and the right portion represents the person image (area H) in FIG. 13. In this manner, by using diagnostic images with different arrangement, it is possible to check that the eye gaze of the subject does not depend on the left-right positional relationship, and to perform more precise diagnosis.

The area 11B is an area including a center of the whole geometric pattern within the area K. The area 12A is an area including a face of a first person (girl). The area 13A is an area including a face of a second person (mother).

In a case where measurement is performed to determine whether the subject is interested in a person or a geometric pattern, at least one of the area 12A and the area 13A is used as an area for determining that the subject is interested in a person. Additionally, the area 11B is used as an area for determining that the subject is interested in a geometric pattern.

In FIGS. 12 and 13, the shapes of the determination areas are ellipse (or circle). The shapes of the determination areas are not limited to these but may have arbitrary shapes. For example, although FIG. 12 illustrates an exemplary geometric pattern image including three concentric geometric patterns, the number of geometric patterns may be any number. As described above, the diagnostic image may be a moving image. In this case, it is possible to move the determination area together with the movement of the image. The trajectory of black dots as signs on the diagnostic image represent exemplary trajectories of gaze points detected on the diagnostic image.

Figure 14:
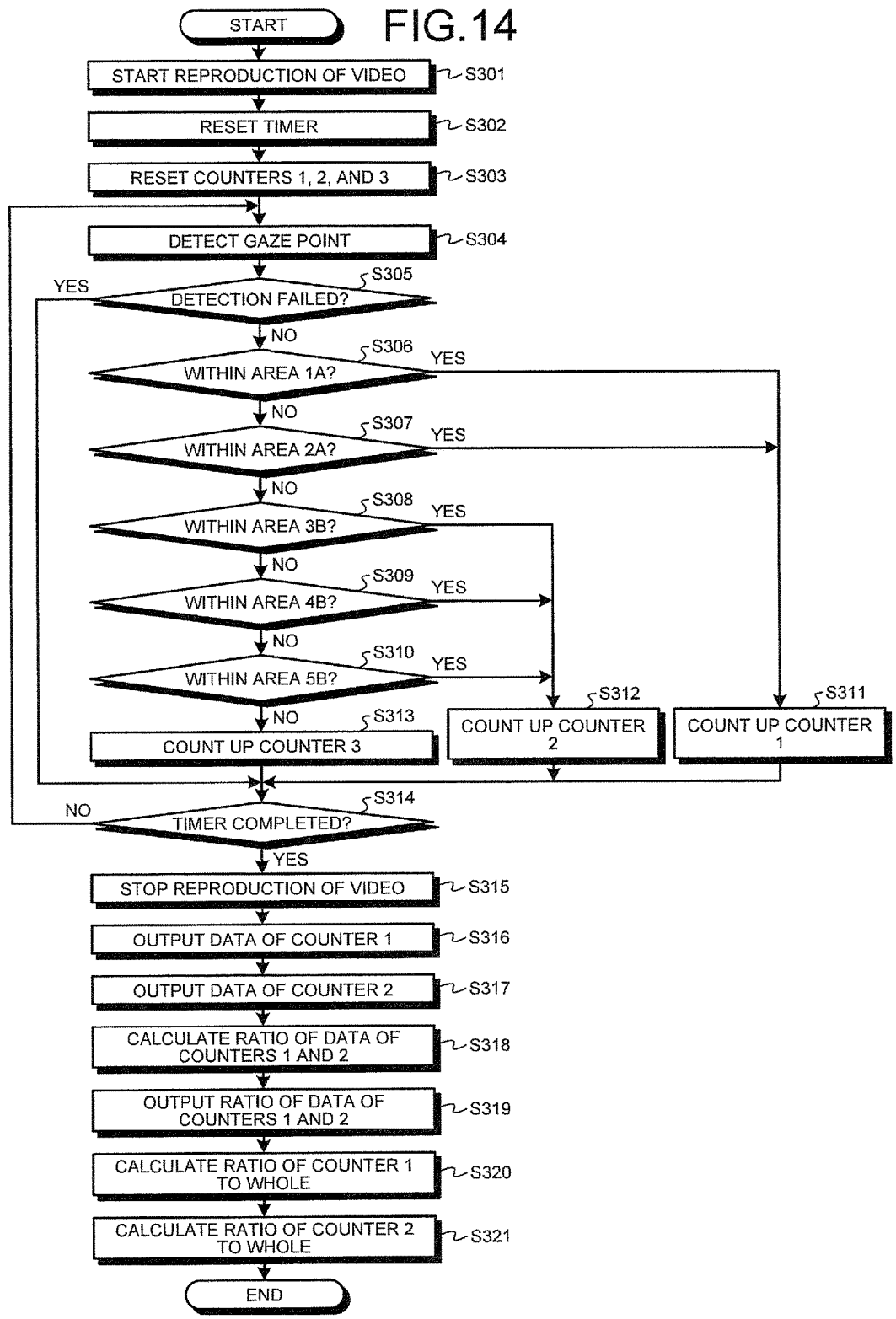
FIG. 14 is a flowchart illustrating exemplary diagnosis assistance processing in a case where the diagnostic image in FIG. 12 is used.

FIG. 14 is a flowchart illustrating exemplary diagnosis assistance processing in a case where the diagnostic image in FIG. 12 is used.

First, the controller 300 starts (step S301) reproduction of an image (video). Next, the controller 300 resets a timer that measures time slightly shorter than the reproduction time of the video (step S302). Next, the controller 300 resets counters 1, 2, and 3 (step S303). The counter 1 counts up when a determination area in a person image obtains a gaze. The counter 2 counts up when a determination area in a geometric pattern image obtains a gaze. The counter 3 counts up in a case where a position besides these areas obtains a gaze.

Gaze point measurement described below is performed, for example, for each frame of the stereo camera that performs imaging in synchronization. In other words, the gaze point is measured at a predetermined time interval. Accordingly, the count values of the counters 1, 2, and 3 correspond to the gazing time. The counter 1 corresponds to the time (gazing time) for which the gaze point (first gaze point) is detected in a determination area in a person image. The counter 2 corresponds to the time (gazing time) for which the gaze point (second gaze point) is detected in a determination area in a geometric pattern image.

Next, gaze point detection is performed (step S304). In accordance with the procedure described in the diagrams up to FIG. 10, for example, gaze point detection is executed by the first calculator 351, the second calculator 352, the third calculator 353, and the eye gaze detector 354. Next, the controller 300 judges whether gaze point detection has failed (step S305). Gaze point detection fails, for example, in a case where images of the pupil and corneal reflection cannot be obtained due to blinking, or the like. Gaze point detection also fails in a case where the gaze point is not within the display screen 201 (in a case where a position other than the display screen 201 is viewed).

In a case where gaze point detection fails (step S305: Yes), processing from steps S306 to S313 is skipped and the processing moves to step S314, so as not to affect the counters 1, 2, and 3.

In a case where the gaze point detection is successful (step S305: No), the controller 300 judges whether the gaze point is within the area 1A based on the coordinates of the obtained gaze point (step S306). When the gaze point is within the area 1A (step S306: Yes), the controller 300 counts up the counter 1 (step S311). In a case where the gaze point is not within the area 1A (step S306: No), the controller 300 judges whether the gaze point is within the area 2A (step S307). When the gaze point is within the area 2A (step S307: Yes), the controller 300 counts up the counter 1 (step S311).

In a case where the gaze point is not within the area 2A (step S307: No), the controller 300 judges whether the gaze point is within the area 3B based on the coordinates of the obtained gaze point (step S308). When the gaze point is within the area 3B (step S308: Yes), the controller 300 counts up the counter 2 (step S312). In a case where the gaze point is not within the area 3B (step S308: No), the controller 300 judges whether the gaze point is within the area 4B (step S309). When the gaze point is within the area 4B (step S309: Yes), the controller 300 counts up the counter 2 (step S312). In a case where the gaze point is not within the area 4B (step S309: No), the controller 300 judges whether the gaze point is within the area 5B (step S310). When the gaze point is within the area 5B (step S310: Yes), the controller 300 counts up the counter 2 (step S312).

In a case where no gaze point exists within any of the determination areas (step S310: No), this means the subject is not viewing either the face of the person or a position around the center of the geometric pattern. Accordingly, the controller 300 counts up the counter 3 (step S313).

Next, the controller 300 checks completion of the timer (step S314) in order to check completion of the video. For example, the controller 300 determines that the timer has completed in a case where the timer value reaches a predetermined value that corresponds to the completion time of the video. In a case where the timer is not completed (step S314: No), processing returns to step S304 and repeats the processing.

In a case where the timer is completed (step S314: Yes), the controller 300 stops reproduction of the video (step S315). Next, the controller 300 outputs data of the counter 1 (step S316). The data of the counter 1 corresponds to the gazing time on the determination area in the person image. Next, the controller 300 outputs data of the counter 2 (step S317). The data of the counter 2 corresponds to the gazing time on the determination area in the geometric pattern.

Next, the evaluator 357 calculates ratios of the counter 1 and the counter 2 (step S318). The ratios in this case include the ratio of a count value of the counter 1 to a count value of the counter 2, the ratio of a count value of the counter 2 to a count value of the counter 1, the ratio of a count value of the counter 1 to the sum of the count value of the counter 1+count value of the counter 2, or the ratio of a count value of the counter 2 to the sum of the count value of the counter 1+count value of the counter 2. Evaluation values like these can be an index of possibility of developmental disorder. The higher the ratio of gazing at the determination area in the geometric pattern, the higher the possibility of developmental disorder. The evaluator 357 outputs the calculated evaluation value (ratio data) (step S319).

Next, the evaluator 357 calculates (step S320) the ratio of the count value of the counter 1 to the count values regarding all gaze points used for evaluation (count value of counter 1+count value of counter 2+count value of counter 3). The higher the value, the even lower the possibility of developmental disorder.

Next, the evaluator 357 calculates (step S321) the ratio of the count value of the counter 2 to the count values regarding all gaze points used for evaluation (count value of counter 1+count value of counter 2+count value of counter 3). The higher the value, the even higher the possibility of developmental disorder.

Calculation methods of the evaluation value are not limited to the above-described methods. It is appropriate to use any evaluation value as long as the value leads to determination which of the images, namely, the person image or the pattern image, obtains the gaze. In an example of FIG. 14, three evaluation values are calculated (steps S318, S320, and S321), although the number of evaluation values to calculate is arbitrary.

In this manner, in the present embodiment, a partial area in each of the person image and the geometric image is determined as a gaze point detection target (diagnosis target), instead of the entire person image and the geometric image (e.g. area H and area K). With this configuration, it is possible to avoid, for example, erroneously detecting the gaze point in a case where the gaze point accidentally falls in the area without intension of gazing. Accordingly, it is possible to enhance accuracy of detection (diagnosis).

Figure 15:
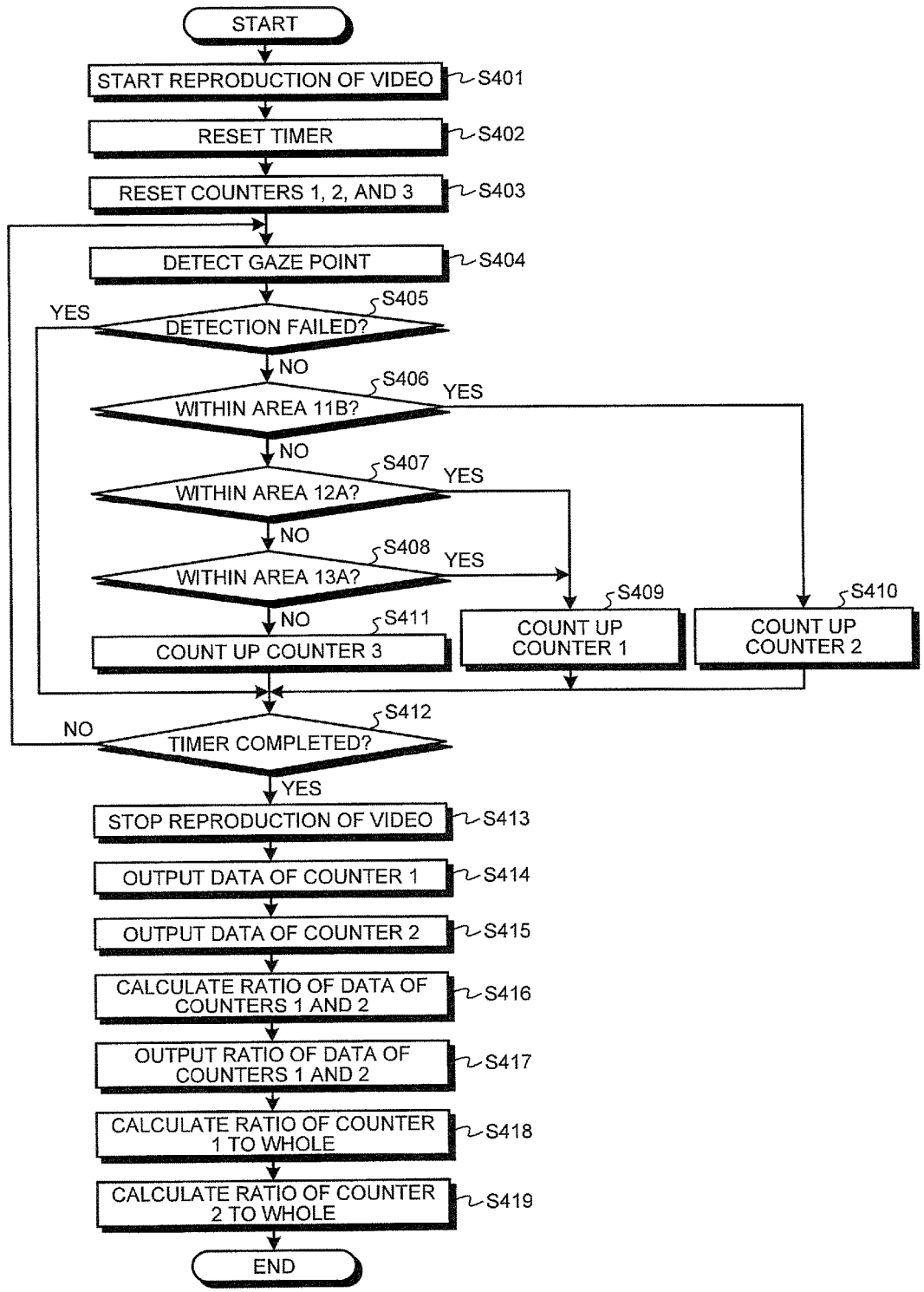
FIG. 15 is a flowchart illustrating exemplary diagnosis assistance processing in a case where the diagnostic image in FIG. 13 is used.

FIG. 15 is a flowchart illustrating exemplary diagnosis assistance processing in a case where the diagnostic image in FIG. 13 is used.

Since steps S401 to S405 are similar to steps S301 to S305 illustrated in FIG. 14, the description thereof will be omitted.

In a case where the gaze point detection is successful, the controller 300 judges whether the gaze point is within the area 11B based on the coordinates of the obtained gaze point (step S406). When the gaze point is within the area 11B (step S406: Yes), the controller 300 counts up the counter 2 (step S410).

In a case where the gaze point is not within the area 11B (step S406: No), the controller 300 judges whether the gaze point is within the area 12A (step S407). When the gaze point is within the area 12A (step S407: Yes), the controller 300 counts up the counter 1 (step S409). In a case where the gaze point is not within the area 12A (step S407: No), the controller 300 judges whether the gaze point is within the area 13A (step S408). When the gaze point is within the area 13A (step S408: Yes), the controller 300 counts up the counter 1 (step S409).

In a case where no gaze point exists within any of the determination areas (step S408: No), this means the subject is not viewing either the face of the person or a position around the center of the geometric pattern. Accordingly, the controller 300 counts up the counter 3 (step S411).

Since steps S412 to S419 are similar to steps S314 to S321 illustrated in FIG. 13, the description thereof will be omitted.

The determination area provided in the person image is not limited to the area including a face portion. Similarly, the determination area provided in the geometric pattern image is not limited the area including the center of the geometric pattern. Any area in each of the images can be used as long as it is an area having a significant difference in the gazing time between the neurotypical subject and the subject with developmental disorder.

For example, in a case where the image of the face portion is large, it is appropriate to define the area including the eye in the person image as the determination area. It is also appropriate to define an area including a characteristic portion of the geometric pattern, an area including a portion in which density of lines forming the geometric pattern is higher than other portions, an area including a portion in which the geometric pattern changes, or the like, in a geometric pattern image, as the determination area.

Figure 16:
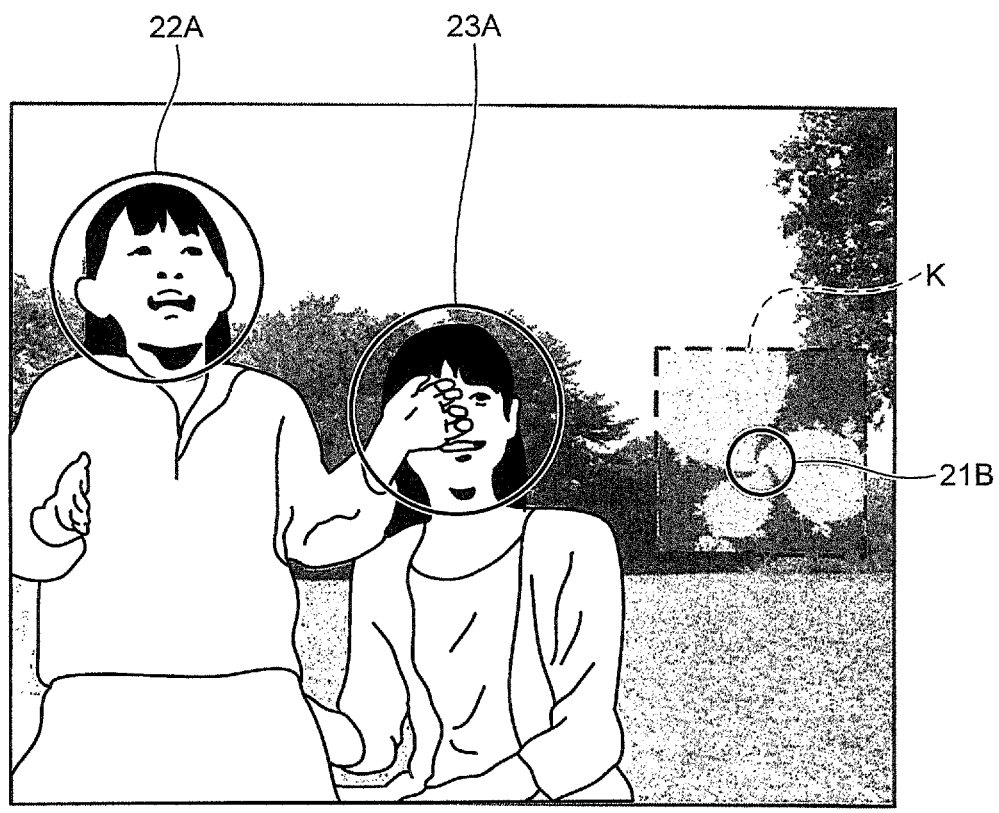
FIG. 16 is a diagram illustrating another exemplary diagnostic image used in the present embodiment.

The diagnostic image is not limited to the image in which a person image and a geometric pattern image are arranged side by side but may be any image as long as the image includes a person image and a geometric pattern image. FIG. 16 is a diagram illustrating another exemplary diagnostic image used in the present embodiment. FIG. 16 is an exemplary diagnostic image that includes a person image in a range from the center to the left portion and includes a geometric pattern image (area K) in the right portion. Areas 22A and 23A are determination areas in the person image. An area 21B is a determination area in the geometric pattern image. In a case where the diagnostic image in FIG. 16 is used, it is appropriate to execute, for example, the diagnosis assistance processing in FIG. 15 by using the areas 22A, 23A and 21B instead of the areas 12A, 13A, and 11B in FIG. 13.

In the diagnostic image, a determination area is provided in each of the person image or geometric pattern image. Alternatively, it is also appropriate to detect gaze points by configuring separately, namely, as for the person image, a determination area is provided in the person image, and as for the geometric pattern image, the entire geometric pattern image is defined as a determination area. As yet another alternative, it is also appropriate to detect gaze points by configuring such that, as for the person image, the entire person image is defined as a determination area, and as for the geometric pattern image, a determination area is provided in the geometric pattern image. By providing a determination area in at least one of the images, it is possible to enhance accuracy in detecting the gaze point.

As stated above, the following effects can be obtained, for example, according to the present embodiment.

(1) In contrast to a known method that compares the gazing time for viewing the entire person image with the gazing time for viewing the entire geometric pattern image, there is more significant difference in gazing time (evaluation result) between a neurotypical subject and a subject with developmental disorder. Accordingly, it is possible to achieve higher sensitivity and specificity.

(2) There is no need to dispose a light source (illuminator) at two positions, making it possible to detect an eye gaze using a light source disposed at a single position.

(3) Arranging the light source at a single position makes it possible to miniaturize the apparatus and reduce the cost.

The entire content of Japanese Patent Application No. 2014-062183 (filing date: Mar. 25, 2014) and Japanese Patent Application No. 2014-062184 (filing date: Mar. 25, 2014) is incorporated herein by reference.

REFERENCE SIGNS LIST

100 DIAGNOSIS ASSISTANCE APPARATUS
101 DISPLAY
102 STEREO CAMERA
103 LED LIGHT SOURCE
150 STORAGE
201 DISPLAY SCREEN
202 RIGHT CAMERA
203 LEFT CAMERA
205 SPEAKER
300 CONTROLLER
313 DRIVE/IF
316 LED DRIVE CONTROL UNIT
322 SPEAKER DRIVE
351 FIRST CALCULATOR
352 SECOND CALCULATOR
353 THIRD CALCULATOR
354 EYE GAZE DETECTOR
355 GAZE POINT DETECTOR
356 OUTPUT CONTROLLER
357 EVALUATOR

What is claimed is:

1. A detection apparatus comprising:
   a display;
   an imaging unit configured to image a subject;
   an eye gaze detector configured to detect an eye gaze direction of the subject based on a captured image captured by the imaging unit;
   an output controller configured to display a diagnostic image that includes a person image and a geometric pattern image, onto the display; and
   a gaze point detector configured to:
      set a first determination area at a region including a face portion in the person image,
      detect a first gaze point as a gaze point of the subject in the first determination area based on the eye gaze direction,
      set a second determination area at a region in the geometric pattern image, and
      detect a second gaze point as a gaze point of the subject in the second determination area,
      wherein the first determination area and the second determination area are configured to be set in such a manner that a gazing time difference between a neurotypical subject and a subject with developmental disorder becomes significant.

2. The detection apparatus according to claim 1, further comprising an evaluator configured to calculate an evaluation value of the subject based on the first gaze point and the second gaze point.

3. The detection apparatus according to claim 2,
   wherein the evaluator calculates an evaluation value of the subject based on at least one of a ratio of a count value of the first gaze point to a count value of the second gaze point, a ratio of the count value of the second gaze point to the count value of the first gaze point, a ratio of the count value of the first gaze point to count values of all gaze points used in evaluation, and a ratio of the count value of the second gaze point to the count values of all the gaze points used in evaluation.

4. The detection apparatus according to claim 1, further comprising:
   an illuminator that includes a light source to emit light;
   a first calculator configured to calculate a first position representing a pupil center based on an image of an eyeball of a subject, the image being captured by the imaging unit with light being emitted from the illuminator;

a second calculator configured to calculate a second position representing a corneal reflection center based on the captured image of the eyeball; and a third calculator configured to calculate a third position representing a corneal curvature center based on a line that connects the light source with the second position, wherein the eye gaze detector detects an eye gaze of the subject based on the first position and the third position.

5. The detection apparatus according to claim 1, wherein the first determination area and the second determination area are moved together with a movement of the diagnostic image.

6. A detection method comprising:

detecting an eye gaze direction of a subject based on a captured image captured by an imaging unit configured to image the subject;

displaying a diagnostic image that includes a person image and a geometric pattern image, onto a display;

setting a first determination area at a region including a face portion in the person image;

detecting a first gaze point as a gaze point of the subject in the first determination area based on the eye gaze direction;

setting a second determination area at a region in the geometric pattern image; and detecting a second gaze point as a gaze point of the subject in the second determination area, wherein the first determination area and the second determination area are configured to be set in such a manner that a gazing time difference between a neurotypical subject and a subject with developmental disorder becomes significant.

* * * * *